United States Patent [19]
Miller et al.

[11] Patent Number: 5,658,243
[45] Date of Patent: Aug. 19, 1997

[54] KNEE BRACE

[75] Inventors: John J. Miller, Easton; John E. Sceppa, Brocton, both of Mass.

[73] Assignee: Boston Brace International, Inc., Avon, Mass.

[21] Appl. No.: 520,467

[22] Filed: Aug. 28, 1995

[51] Int. Cl.$^6$ ........................................................ A61F 5/00
[52] U.S. Cl. ................................................. 602/26; 602/16
[58] Field of Search ................................. 602/5, 16, 23, 602/26

[56] References Cited

U.S. PATENT DOCUMENTS

| | | | |
|---|---|---|---|
| 3,902,482 | 9/1975 | Taylor | 602/26 X |
| 4,337,764 | 7/1982 | Lerman . | |
| 4,387,709 | 6/1983 | Shen . | |
| 4,393,542 | 7/1983 | Martinez . | |
| 4,599,998 | 7/1986 | Castillo . | |
| 4,699,129 | 10/1987 | Aaserude et al. . | |
| 4,732,143 | 3/1988 | Kausek et al. . | |
| 4,733,656 | 3/1988 | Marquette . | |
| 4,773,404 | 9/1988 | Townsend . | |
| 4,986,264 | 1/1991 | Miller . | |
| 5,107,824 | 4/1992 | Rogers et al. | 602/26 X |
| 5,277,698 | 1/1994 | Taylor | 602/26 |
| 5,302,169 | 4/1994 | Taylor | 602/26 X |
| 5,356,370 | 10/1994 | Fleming | 602/26 X |
| 5,400,806 | 3/1995 | Taylor | 602/26 X |
| 5,542,774 | 8/1996 | Hoy | 602/16 X |

Primary Examiner—Linda C. Dvorak
Attorney, Agent, or Firm—Kriegsman & Kriegsman

[57] ABSTRACT

A knee brace comprises an anterior femoral shell conforming to the shape of the upper leg of a person, an anterior tibial shell conforming to the shape of the lower leg of the person, and a posterior calf cuff conforming to the shape of the lower leg of the person. The knee brace further includes first and second mechanical hinges positioned on the medial and lateral sides of the knee of the person, respectively. The first mechanical hinge comprises an upper bar having an upper end fixedly mounted to the femoral shell and a lower end, a center link member pivotally mounted on the lower end of the femoral shell, and a lower bar having a lower end fixedly mounted to the tibial shell and an upper end pivotally mounted on the center link member. The construction of the first mechanical hinge provides for anterior-posterior and rotational movement of the lower bar relative to the upper bar, the exact path of movement of the lower bar relative to said upper bar closely following the natural motion of the knee joint of the person. The second mechanical hinge comprises an upper bar having an upper end fixedly mounted to said femoral shell and a lower bar having a lower end fixedly mounted to the calf cuff. The upper end of the lower bar is pivotally interconnected to the lower end of the upper bar so as to provide for anterior-posterior movement of the lower bar relative to the upper bar. The knee brace additionally includes straps for holding the femoral shell in place on the upper leg of the person and straps for holding the tibial shell and the calf cuff in place on the lower leg of the person.

9 Claims, 8 Drawing Sheets

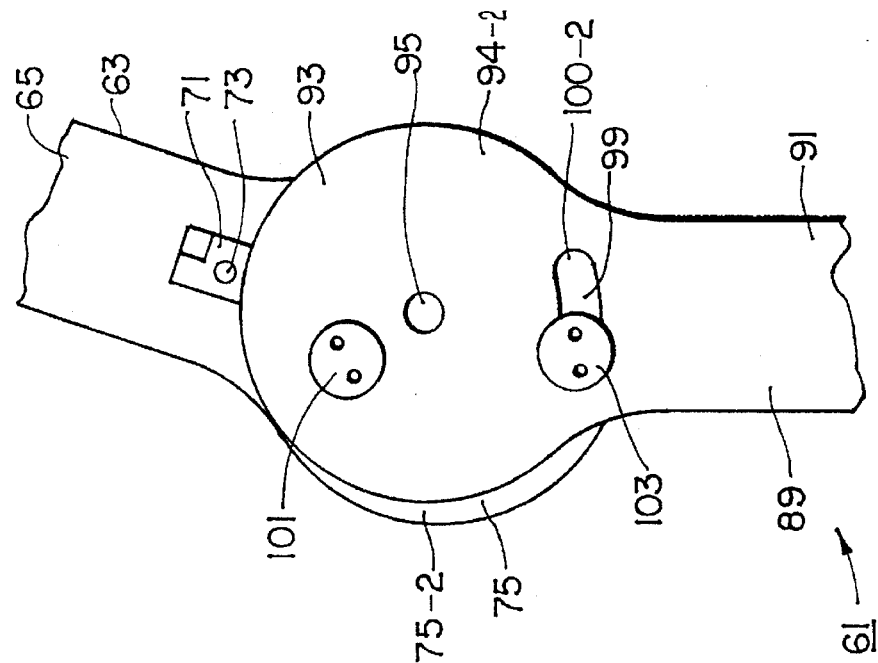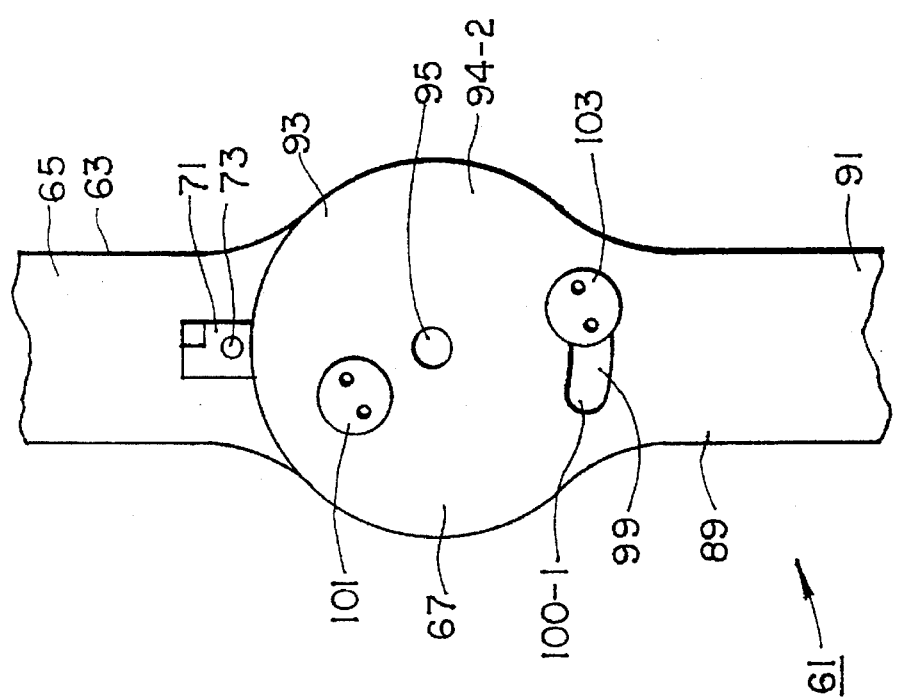

KNEE BRACE

BACKGROUND OF THE INVENTION

The present invention relates generally to orthotics and more specifically to a knee brace for providing support for the knee of a person.

Knee braces for providing support for the knee of a person are well known in the art. Such braces generally include a tibial shell which is constructed so as to be closely configured to the shape of the lower leg and a femoral shell which is constructed so as to be closely configured to the shape of the thigh area of the leg. The two shells are secured to their respective areas on the leg and are interconnected by some type of mechanism so as to pivot relative to each other as the knee is bent. The mechanism is usually a pair of hinge joints, one on each side of the knee brace, with the tibial shell usually being attached to the lower part of each one of the two knee joints and the femoral shell usually being attached to the upper part of each one of the two hinge joints.

Knee braces are often utilized by people who have suffered a knee injury and require some means of protection against further aggravation of the knee during rehabilitation. A knee brace can limit the amount of damage to an injured knee by providing the patient with adequate knee stabilization and control. Stabilization and control is achieved in such a manner as to permit the patient relative freedom in the normal use of the knee joint while, at the same time, permitting control over the joint so as to optimize healing.

In addition, knee braces are often employed by a person having previously suffered a knee injury who wishes to actively participate in strenuous and demanding physical activity. In such cases where the person seeks knee support in furtherance of activities involving heavy running or sprinting, it is extremely advantageous to design a knee brace which most accurately simulates the true motions of the anatomical knee joint. Where a knee brace fails to adequately correspond to the actual motion of the human knee joint, the knee brace will tend to ride down the leg of the person after limited use and will generate more force through the knee capsule, thereby exposing the patient to increased risk of further injury to the knee.

In the past, a number of attempts have been made to create a knee brace which moves with a simple gliding motion and which accurately parallels the intricate movement of the knee joint. However, the motion of the human knee joint in its stages of flexion and extension are quite complex; therefore, attempting to create a knee brace which can properly duplicate the motion of a knee joint has been met with substantial difficulty. First, the movements of flexion and extension in the knee joint differ from those in a typical hinged joint, such as the elbow or hip. The axis around which motion takes place in the knee joint is not fixed, but rather the axis shifts forward during extension, as the gliding movement is superimposed on the rolling motion and the axis shifts backwards during flexion.

In U.S. Pat. No. 4,699,129 to G. V. Aaserude et al, which issued on Oct. 13, 1987, there is disclosed a polycentric variable axis pivotal hinge system especially designed and adaptable to follow the complex movement of the knee when incorporated in a knee brace, the hinge having an upper and a lower extension overlying a central linking member and pivotally connected thereto wherein each extension moves in a relative angular motion determined by the coaction of a guide pin follower slidably and pivotally interacting with slots in the angular terminal portions of the extensions and the guide pin follower moving in a vertical slot in the central member; with provision for motion limiting stops. Although generally useful, it should be noted that a polycentric variable axis hinge such as shown in U.S. Pat. No. 4,699,129 has certain drawbacks. For instance, when incorporated in a knee brace, the aforementioned hinge fails to provide for rotational movement of the knee joint. In particular as the knee goes into flexion, the tibia will rotate about a vertical axis through the knee joint. Similarly, when the knee is straightened, the knee joint will generally rotate in the Opposite direction, usually along the same path the knee joint moved in the stages of flexion. Generally, the rotation of the knee joint occurs during the first 25 degrees of flexion; however, the pattern of rotation and anterior-posterior flexion in the knee joint can vary considerably between any two people. Therefore, it is desirable that any knee joint which is implemented in a knee brace be able to accommodate the different paths of rotation as well as anterior-posterior movement of the tibia relative to the femur in knee joints of a broad spectrum of people. The above-described hinge fails to accommodate the natural tendency for the leg to rotate, and therefore will disrupt the knee joint's natural motion. As a consequence, this hinge will inadequately represent the motion of the knee joint and consequently, the drawbacks enumerated above will potentially develop.

In U.S Pat. No. 4,986,264 to M. E. Miller, there is disclosed a knee brace having an anterior tibial shell and an anterior femoral shell which are closely configured to the shape of the lower leg and thigh respectively and which are joined by a frame in the form of a pair of polycentric hinge joints. Each one of the joints includes an upper bar and a lower bar, the two bars being pivotally interconnected. The anterior tibial shell and the anterior femoral shell are both pivotally mounted on the upper bars of the polycentric hinge joints, the anterior femoral shell being mounted above the anterior tibial shell. Because the anterior tibial shell is mounted on the upper bars of the two joints when the knee brace is mounted on the leg of a person and the knee is bent the anterior tibial shell will move downward and inward against the tibia so as to counteract forward directed forces applied to the tibia and thereby provide additional support for the knee. The knee brace also includes a pair of derotation cuffs removably mounted on the femoral and tibial shells for internally rotating the femur and externally rotating the tibia, respectively.

In U.S. Pat. No. 4,733,656 to S. Marquette there is disclosed a knee brace having an anterior tibial shell and a posterior femoral shell which are closely configured to the shape of the lower and thigh areas of the leg, the two shells being joined by a closed support band system which is constructed to closely tract knee flexion. The band system includes upper vertical uprights and lower vertical uprights which are pivotally interconnected to each other. The femoral shell is attached to the upper vertical uprights while the tibial shell is attached to the lower vertical uprights. The brace also has anteriorly extending tabs positioned between the patella and the femoral epicondyles. The combination of two shells, the band system and the two tabs provides anterior-posterior, medial-lateral and rotary stability.

In U.S. Pat. No. 4,773,404 to J. H. Townsend there is disclosed an appliance for controlling an unstable knee joint in the sagittal, coronal and transverse planes, comprising femoral and tibial cuffs joined by femoral and tibial links which are interconnected to provide a novel mechanical joint wherein camming slots are formed in one of the links with cams disposed on the other link, the slots comprising straight segments and arcuate segments so as to provide approximately 8 millimeters of sliding movement between the femur and the tibia, followed by relative rotation about the center of radius of the femoral condyle as the leg is flexed. The tibial cuff is conformed about the bony prominence or shin or the tibia to inhibit rotation of the leg beneath the knee within the brace itself.

Other patents of interest include U.S. Pat. No. 4,732,143 to J. Kausek et al, U.S. Pat. No. 4,599,998 to J. D. Castillo, U.S. Pat. No. 4,393,542 to G. Martinez, U.S. Pat. No. 4,387,709 to C. A. Shen, and U.S. Pat. No. 4,337,764 to M. Lerman.

SUMMARY OF THE INVENTION

It is an object of the present invention to provide a new and improved orthopedic appliance.

It is another object of the present invention to provide a new and improved knee brace.

It is yet another object of the present invention to provide a knee brace which accurately duplicates the complex motion of the knee joint.

It is still another object of the present invention to provide a knee brace which permits the tibia to rotate relative to the femur about a vertical axis in the knee joint during flexion or extension.

It is yet another object of the present invention to provide a knee brace hinge that allows for both anterior-posterior movement of the tibia relative to the femur along a vertical plane and rotational movement of the tibia relative to the femur about a vertical axis in the knee joint.

It is still another object of the present invention to provide a knee brace which can be mass produced, has a minimal number of parts, and can be easily assembled.

According to one feature of the invention there is provided an knee brace for providing support of the knee of a person, the knee brace including an anterior femoral shell conforming to the shape of the upper leg of the person, an anterior tibial shell conforming to the shape of the lower leg of the person, a posterior calf cuff conforming to the shape of the lower leg of the person, a first mechanical hinge positioned on the medial side of the knee of the person, said first mechanical hinge comprising an ,upper bar having an upper end and a lower end and a lower bar having an upper end and a lower end, the upper end of the upper bar being fixedly mounted to said anterior femoral shell, the lower end of the lower bar being fixedly mounted to said anterior tibial shell, and the upper end of the lower bar being pivotly interconnected to the lower end of the upper bar so as to provide anterior-posterior movement of the lower bar relative to the upper bar and rotational movement of the lower bar relative to the upper bar, a second mechanical hinge positioned on the lateral side of the knee of the patient, said second mechanical hinge comprising an upper bar having an upper end and a lower end and a lower bar having an upper end and a lower end, the upper end of the upper bar being fixedly mounted to said anterior femoral shell, the lower end of the lower bar being fixedly connected to said posterior calf cuff, and the upper end of the lower bar being pivotly interconnected to the lower end of the upper bar so as to provide anterior-posterior movement of the lower bar relative to the upper bar, means for holding said anterior femoral shell in place on the upper leg of the person, means for holding said anterior tibial shell in place on the lower leg of the person, and means for holding said posterior calf cuff in place on the lower leg of the person.

According to another feature of the present invention, the first mechanical hinge of the knee brace includes an upper bar having an upper end and a lower end, the lower end having a hole to receive a first pivot pin, a center link member overlying the lower end of said upper bar, said center link having a convex top surface and including a hole to receive a first pivot pin, a hole to receive a second pivot pin, and a hole to receive a first stop pin, a first pivot pin extending through the hole to receive a first pivot pin in said upper bar and the hole to receive a first pivot pin in said center link member, said first pivot pin enabling anterior-posterior movement of said center link member relative to said upper bar, a lower bar having an upper end and a lower end, the upper end having a concave bottom surface overlying said convex top surface of said center link member, the upper end of the lower bar having a hole to receive a second pivot pin and a slot, a second pivot pin extending through the hole to receive a second pivot pin in said lower bar and the opening to receive a second pivot pin in said center link member, said second pivot pin enabling rotational movement of said lower bar relative to said central link member, and a first stop pin extending through the slot in said lower bar and the hole to receive a first stop pin in said center link member, said first stop pin limiting the range of rotational movement of said lower bar relative to said central link member.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration a specific embodiment for practicing the invention. This embodiment will be described in sufficient detail to enable those skilled in the art to practice the invention, and it is to be understood that other embodiments may be utilized and that structural changes may be made without departing from the scope of the invention. The following derailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate an embodiment of the invention and, together with the description, serve to explain the principles of the invention. In the drawings wherein like reference numerals represent like parts:

FIGS. 7 and 8 are fragmentary plan views of the mechanical hinge shown in FIG. 5 at two different positions;

FIG. 1 is a fragmentary side view of the lower bar in the mechanical hinge shown in FIG. 9.

DETAILED DESCRIPTION OF A PREFERRED EMBODIMENT

Figure 1:
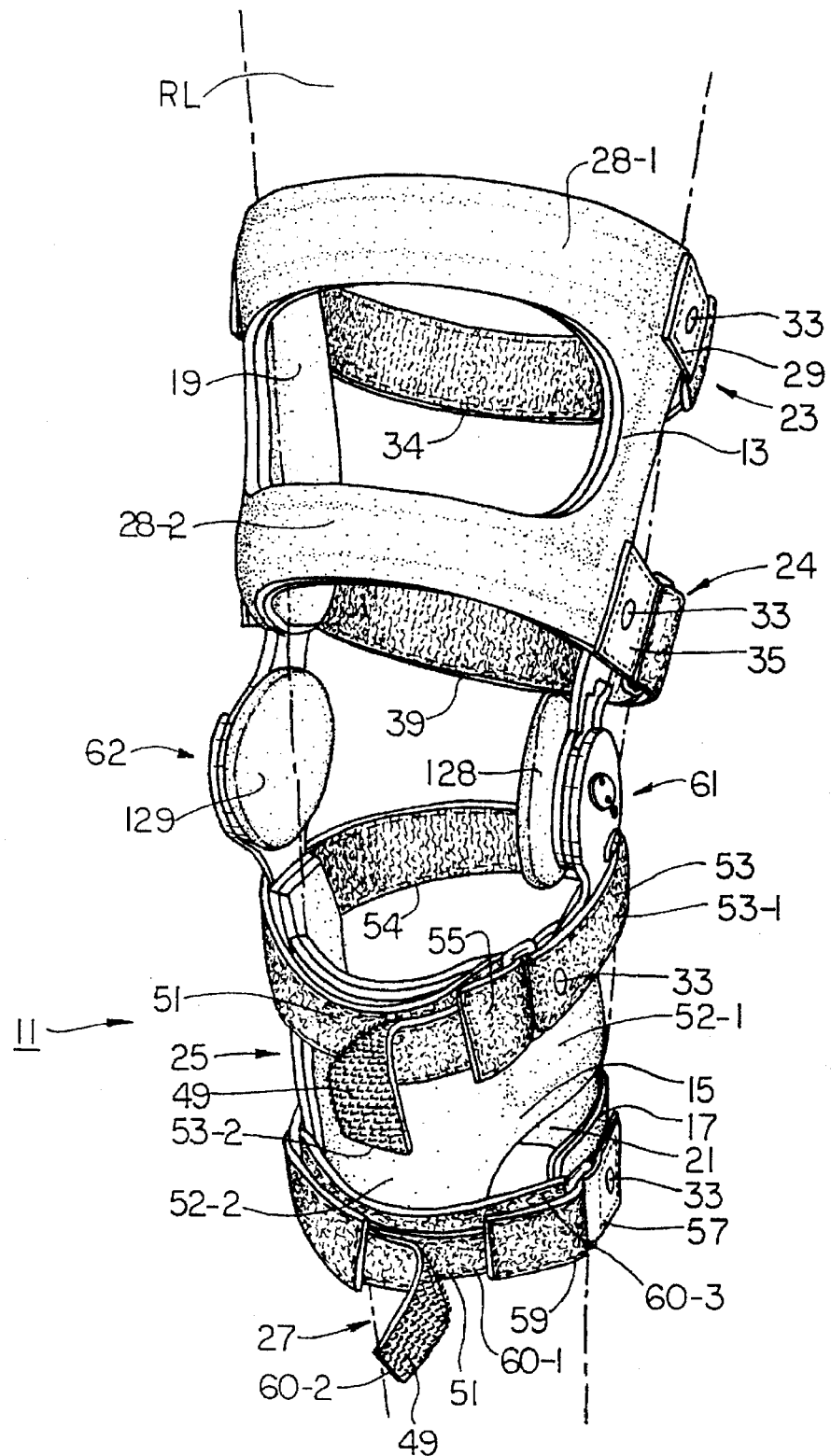
FIG. 1 is a front, right perspective view of a knee brace constructed according to the teachings of the present invention and mounted on the right leg of a wearer, the right leg and knee brace being slightly bent.
Figure 2:
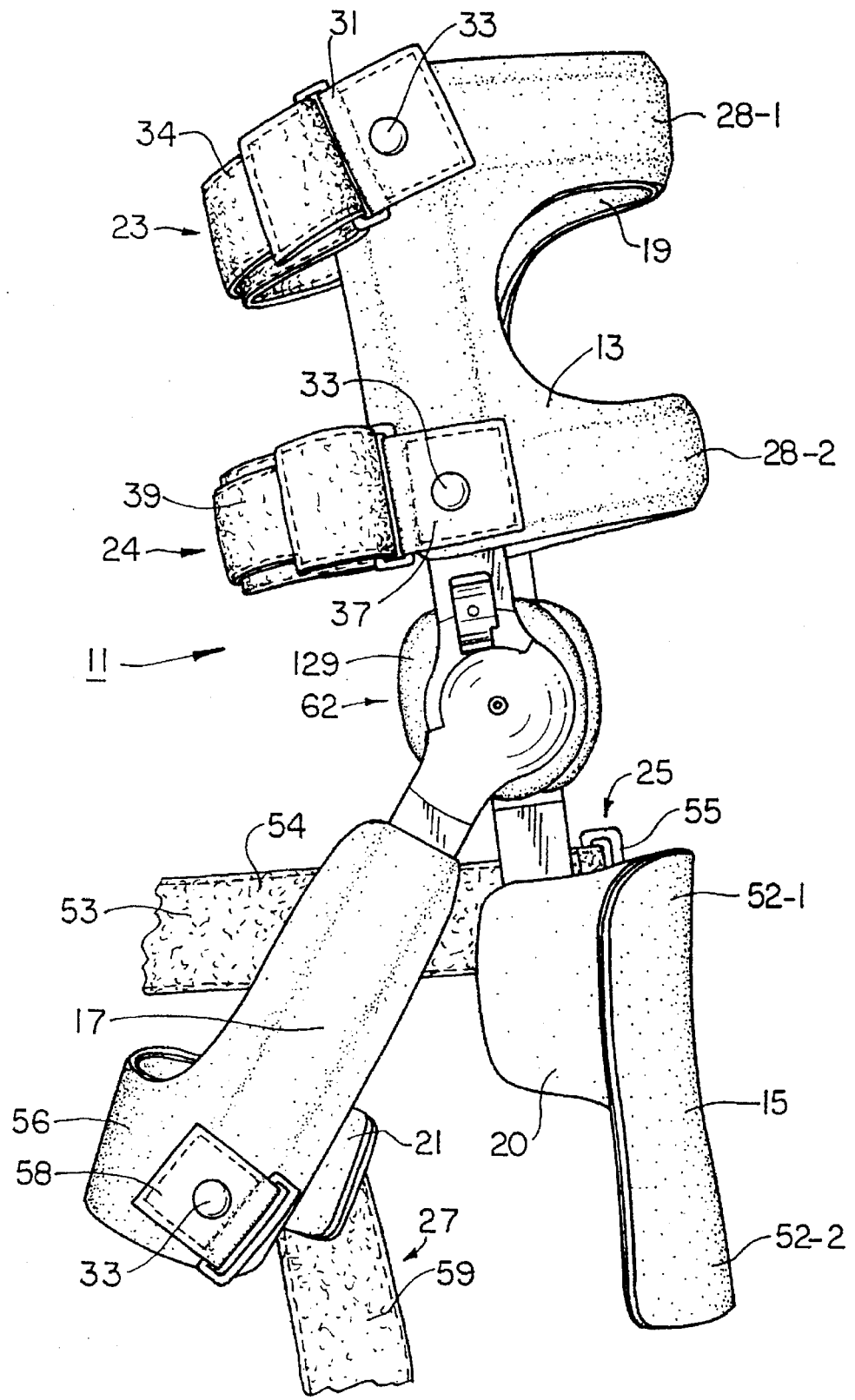
FIG. 2 is a left side view of the knee brace shown in FIG. 1, with the mechanical hinge on the medial side of the knee being fully extended and the mechanical hinge on the lateral side of the knee being fully flexed.
Figure 3:
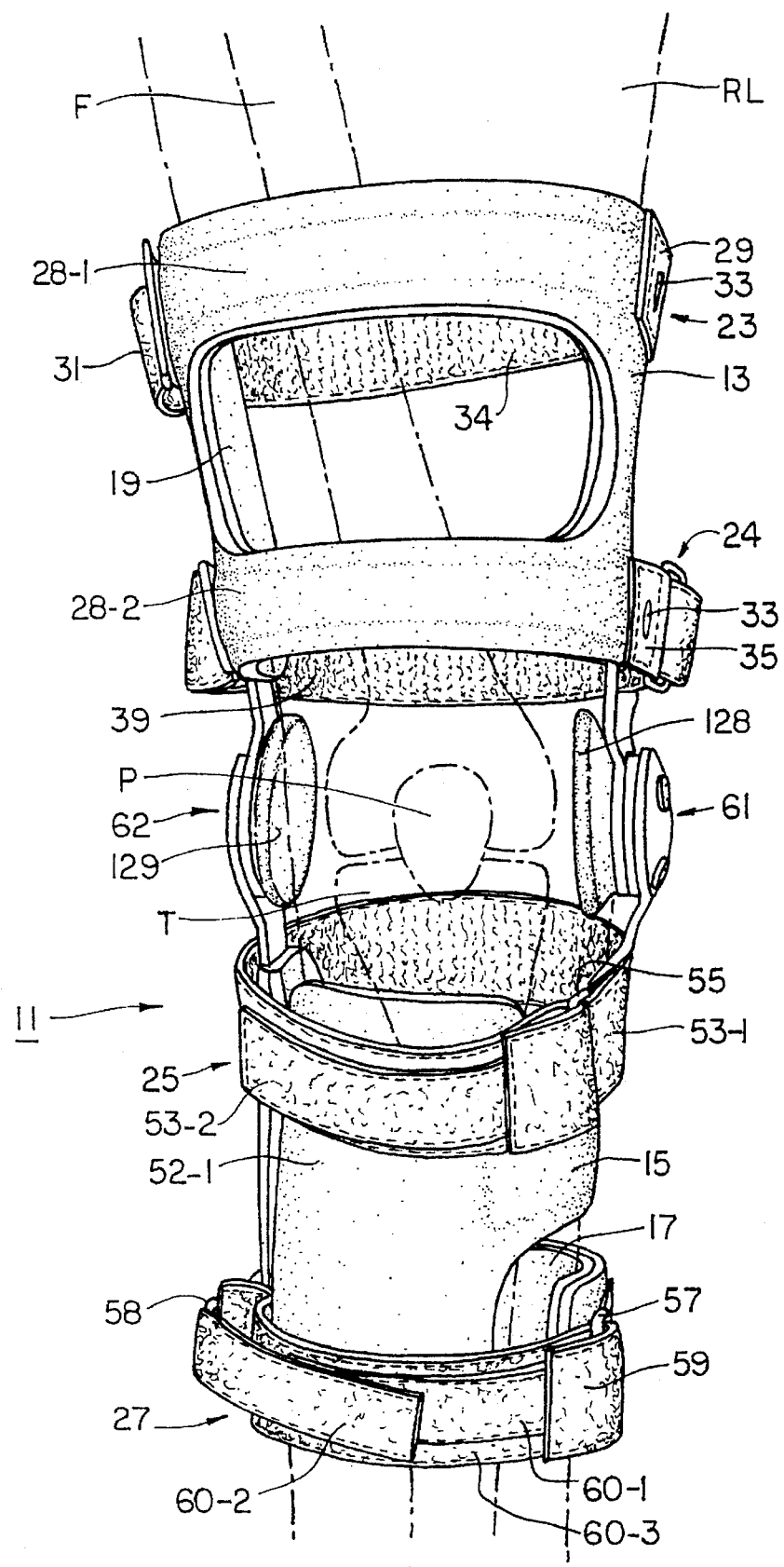
FIG. 3 is a front, perspective view of the knee brace and leg shown in FIG. 1 with the knee brace and leg in a straight position.
Figure 4:
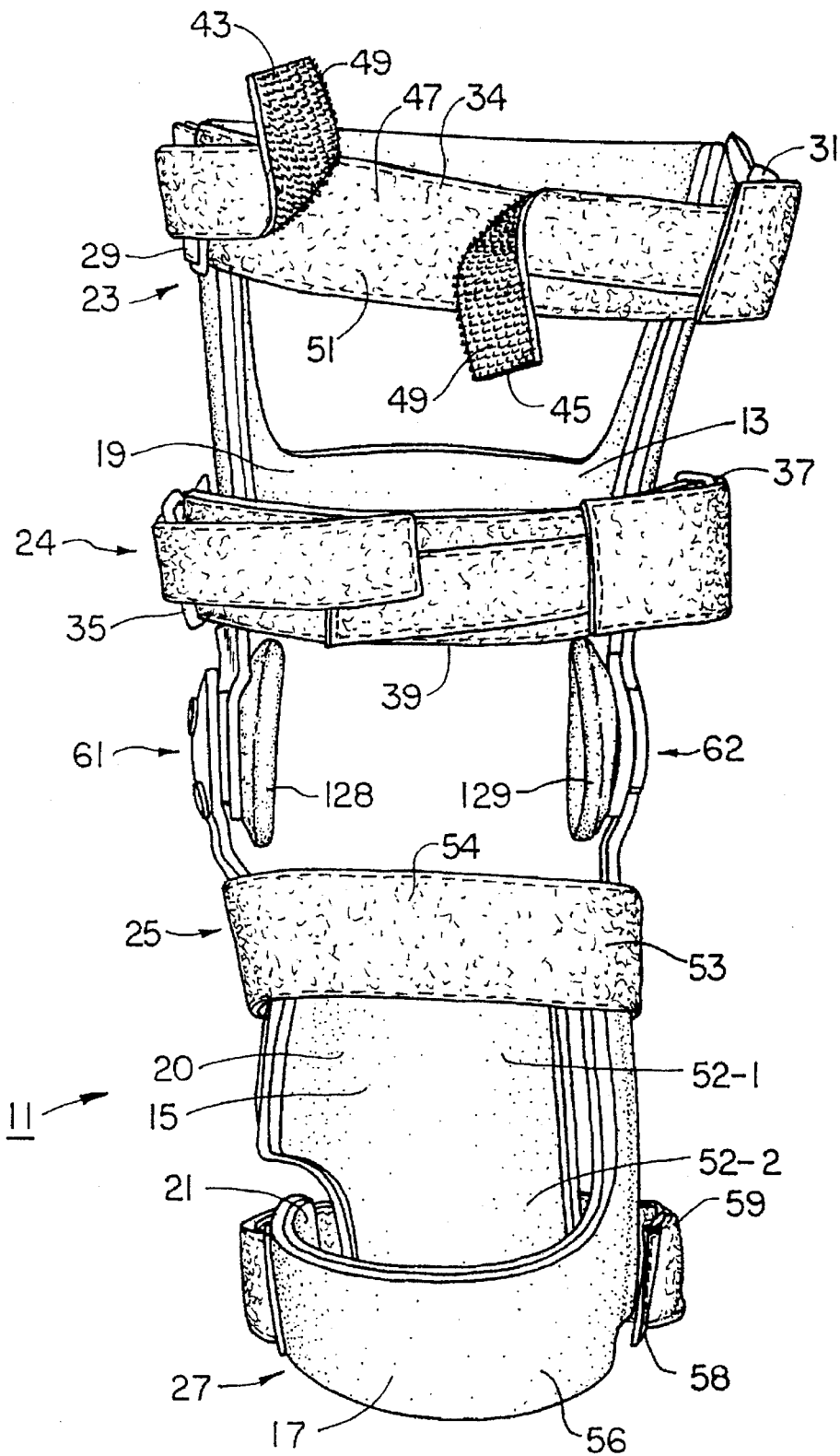
FIG. 4 is a rear view of the knee brace shown in FIG. 1.

Referring now to the drawings, and first to FIGS. 1–4, there is shown a knee brace constructed according to the teachings of the present invention, the knee brace being represented generally by reference numeral 11. Knee brace 11 as shown in the Figures is constructed for use on the right leg RL of a person; however, as will be explained below the invention is not intended to be limited solely to a knee brace for the right leg. A knee brace according to the invention can also be constructed for use on the left leg of a person by simply reversing certain parts as will hereinafter be explained. So that the fit of knee brace 11 may be clearly understood, FIG. 3 also depicts the relative positions of the femur F and the tibia T as well as the patella P, which converge to form a typical knee joint. Those aspects of knee brace 11 not pertinent to the present invention are neither described nor shown herein.

Knee brace 11 includes an anterior femoral shell 13 conforming to the shape of the upper leg of the person, an anterior tibial shell 15 conforming to the shape of the lower leg of the person, and a posterior calf cuff 17 conforming to the shape of the lower leg of the person. Shells 13, 15 and cuff 17 are each made of a relatively rigid material such as carbon fiber reinforced acrylic and are each lined with a layer 19, 20 and 21; respectively, of a material such as rubber or foam in order to increase the comfort of knee brace 11 on the person wearing the brace. Knee brace 11 further includes a pair of strap assemblies 23 and 24 for holding anterior femoral shell 13 in place on the upper leg of the person, a strap assembly 25 for holding anterior tibial shell 15 in place on the lower leg of the person, and a strap assembly 27 for holding posterior calf cuff 17 in place on the lower leg of the person.

Anterior femoral shell 13 is a unitary member having an upper band portion 28-1 and a lower band portion 28-2. Once positioned properly on the thigh area of the person, strap assemblies 23 and 24 hold shell 13 in place on the upper leg of the person. Strap assembly 23 comprises a pair of buckles 29 and 31 which are fixedly secured to the medial and lateral sides, respectively, of upper band portion 28-1 of anterior femoral shell 13, such as by rivets 33, and a strap 34. Strap assembly 24 comprises a pair of buckles 35 and 37 which are fixedly secured to the medial and lateral sides, respectively, of lower band portion 28-2 of anterior femoral shell 13, such as by rivets 33, and a strap 39. Strap 34 is made of flexible hook and pile material, an example of such material being that sold under the trademark "VELCRO". Strap 34 comprises a first end portion 43, a second end portion 45, and a middle portion 47. First and second end portions 43 and 45 are constructed of a hook-type roughened material 49 on its inner surface and a pile-type fibrous material 51 on its outer surface, whereas middle portion 47 is constructed of pile-type fibrous material 51 on both sides thereof. End portions 43 and 45 of strap 34 can be threaded through opposite buckles 29 and 31, respectively, tightened and doubled over itself so that hook-type material 49 contacts pile-type material 51 to effect a lock. Strap 39 is identical to strap 34 and is mounted on buckles 35 and 37 the same way as strap 34 is mounted on buckles 29 and 31.

Anterior tibial shell 15 is a unitary member having an upper portion 52-1 and a lower portion 52-2. Once positioned properly on the lower leg of the person, strap assembly 25 holds shell 15 in place on the lower leg of the person. Strap assembly 25 comprises a strap 53 having a first end 53-1, a second end 53-2, a middle portion 54, and a buckle 55. Strap 53 is constructed of a hook and pile material, an example of a suitable material is that sold under the trademark "VELCRO". Second end 53-2 is constructed of hook-type roughened material 49 on its inner surface and pile-type fibrous material 51 on its outer surface. Middle portion 54 is constructed of pile-type fibrous material 51 on both sides thereof. First end 53-1 of strap 53 passes through buckle 51, is doubled over itself, and is fixed to upper portion 52-1 of shell 15 by a rivet 33. Second end 53-2 can be wrapped around the back of the lower leg of the patient, around the lower end of the lower bar of the second mechanical hinge (which will be discussed further in detail), threaded through buckle 55, tightened, and doubled over itself so that hook-type material 49 contacts pile-type material 51 to effect a lock.

Posterior calf cuff 17 is an arcuate shaped member which conforms to the shape of the calf of a person. Once posterior calf cuff 17 is properly positioned on the calf of the person, strap assembly means 27 holds cuff 17 in place on the lower leg of the person. Strap assembly 27 comprises a pair of buckles 57, 58 which are fixedly secured to the medial and lateral sides, respectively, of band 56, by rivets 33, and a strap 59. Strap 59 is constructed of a hook and pile material, an example of a suitable material is sold under the trademark "VELCRO". Strap 59 comprises a pair of end portions 60-1, 60-2 and a middle portion 60-3. End portions 60-1, 60-2 are constructed of hook-type roughened material 49 on its inner surface and pile-type fibrous material 51 on its outer surface, whereas middle portion 60-3 is constructed of pile-type fibrous material 51 on both sides thereof. End portions 60-1, 60-2 of strap 59 can be threaded through opposite buckles 57, 58, respectively, tightened and doubled over itself so that hook-type material 49 contacts pile-type material 51 to effect a lock. It should be noted that strap 59, when tightened and locked, is positioned over lower portion 52-2 of anterior tibial shell 15.

Knee brace 11 also comprises a first mechanical hinge 61 positioned on the medial side of the knee joint and a second mechanical hinge 62 positioned on the lateral side of the knee joint.

First mechanical hinge 61, see also FIGS. 5–8, comprises an upper bar 63 constructed of a material such as stainless steel or aircraft aluminum alloy. Upper bar 63 includes an upper end 65 and a lower end 67. Upper end 65 of upper bar 63 is fixedly attached to anterior femoral shell 13 by the same rivet 33 used to attach buckle 37 to lower portion 28-2 of anterior femoral shell 13. Lower end 67 of upper bar 63 is disc shaped and has a concave inner surface 68-1 and a convex outer surface 68-2. Lower end 67 has a hole 69 located approximately in the center thereof. A stop pin 71 having a front stop portion 72-1 and a rear stop portion 72-2 is removably mounted in a recess 72-3 formed at the juncture of upper end 65 and lower end 67 of upper bar 63 and held in place by a screw 73 which extends through a hole 73-1 in upper bar 63, a hole 73-2 in rear stop portion 72-2 and is screwed into a threaded hole 73-3 in front stop portion 72-1.

First mechanical hinge 61 further comprises a disc shaped center link member 75 having a concave inner surface 75-1 and a convex outer surface 75-2, concave inner surface 75-1 overlying the convex outer surface 68-2 of lower end 67 of upper bar 63. Center link member 75 is constructed of a material such as stainless steel or aircraft aluminum alloy and has a recess 77 along its periphery, recess 77 having a first end 79-1 and a second end 79-2. Center link member 75 further has an internally threaded hole 81 located approximately in the center thereof, an internally threaded hole 83 located off-center thereof, and an internally threaded hole 85 located approximately the same distance off-center as hole 81 but on the other side thereof, holes 81, 83, and 85 being located along a generally straight line.

Figure 5:
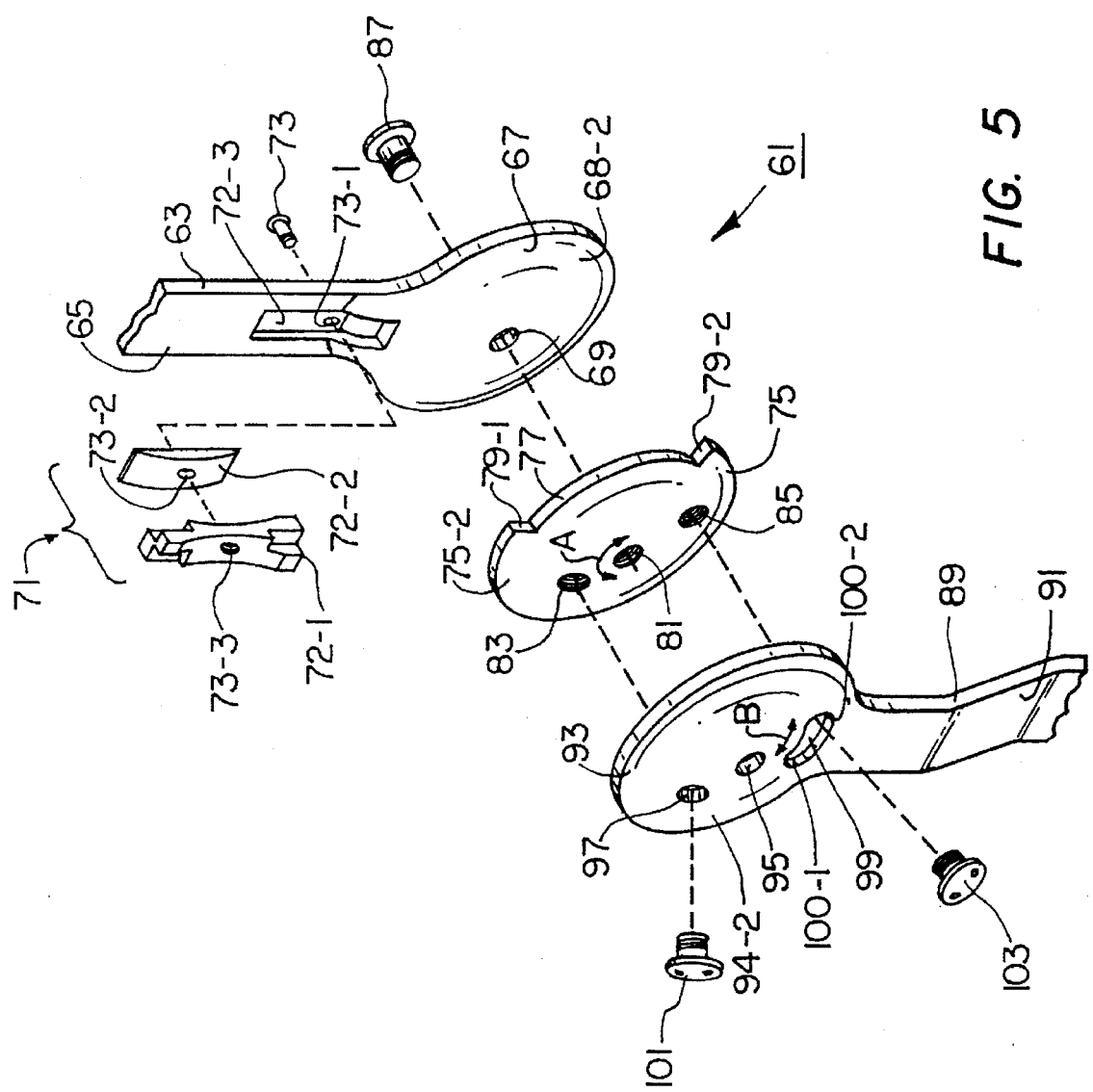
FIG. 5 is an exploded perspective view of the mechanical hinge on the medial side of the knee on the knee brace shown in FIG. 1.
Figure 6:
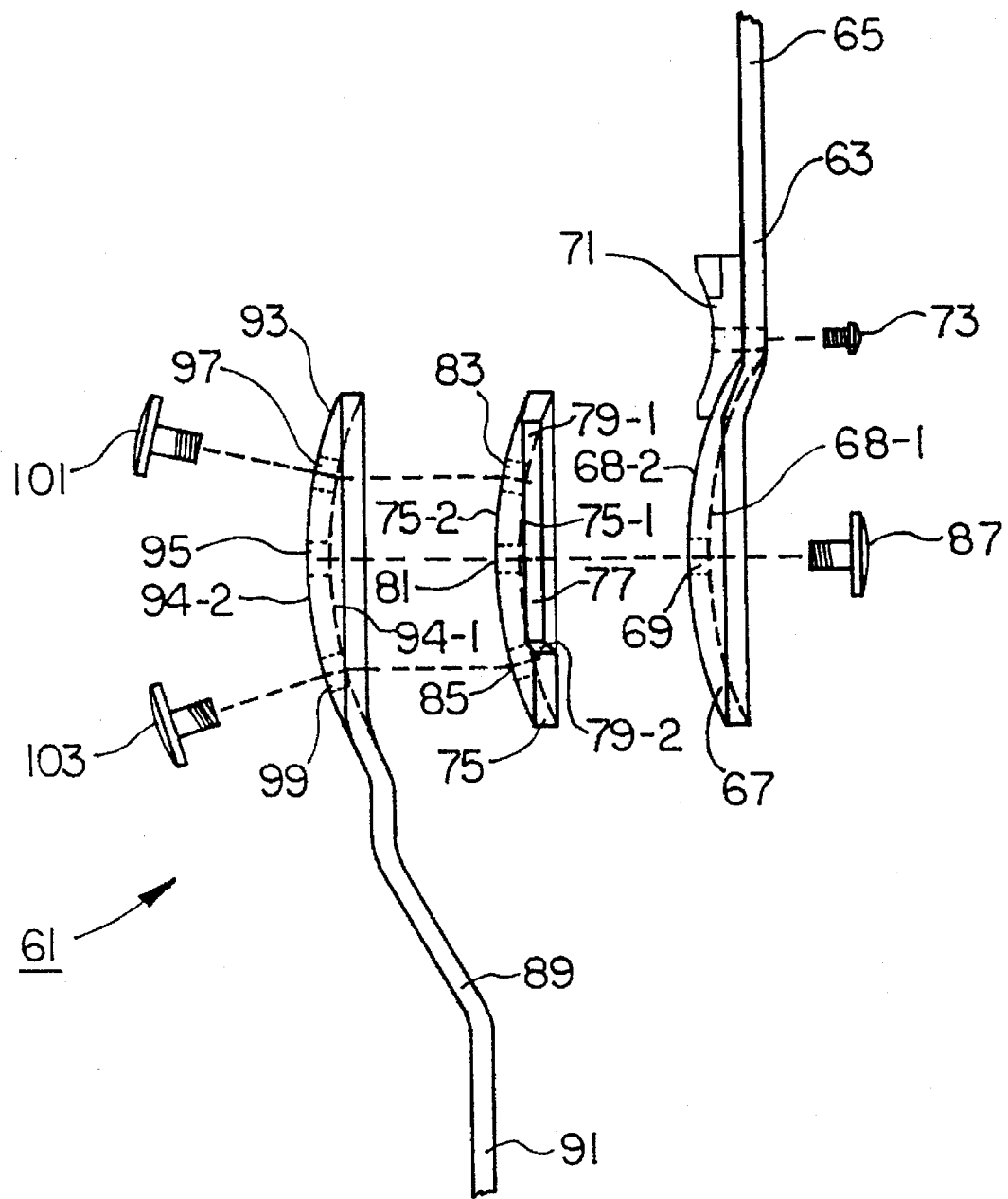
FIG. 6 is a partly exploded side view of the mechanical hinge shown in FIG. 5.

First mechanical hinge 61 further comprises a threaded pivot pin 87 which extends through hole 69 and is screwed into hole 81 so as to pivotally interconnect upper bar 63 to center link member 75 in order to provide for anterior-posterior movement of center link member 75 relative to upper bar 63 in the direction as shown by arrow A in FIG. 5. Stop pin 71 in upper bar 63 is located within recess 77 along the periphery of center link member 75. Upon anterior-posterior movement of center link member 75 relative to upper bar 63, stop pin 71 disposed in recess 77 will effectively limit the range of anterior-posterior movement of upper bar 63 relative to center link 75. Additionally, if desired, stop pin 71 can be replaced with a differently sized stop pin so as to change the range (i.e. limits) of anterior-posterior motion.

First mechanical hinge 61 further comprises a lower bar 89 constructed of a material such as stainless steel or aircraft aluminum alloy. Lower bar 89 comprises a lower end 91 and an upper end 93. Lower end 91 is fixedly mounted on the medial side of anterior tibial shell 15. Upper end 93 is generally disc shaped and includes a concave inner surface 94-1 and a convex outer surface 94-2. Concave inner surface 94-1 of upper end 93 at least partially overlies convex outer surface 75-2 of center link 75 and has a center hole 95, a hole 97 located off-center of center opening 95, and a curved slot 99 located approximately the same distance off-center as hole 97, holes 95, 97, and slot 99 being approximately linear in arrangement. Slot 99 has a first end 100-1 and a second end 100-2. Center hole 95 is used for assembly purposes.

First mechanical hinge 61 further comprises a threaded pivot pin 101 which extends through hole 97 and is screwed into hole 83 in convex outer surface 75-2 of center link 75. Pivot pin 101 enables rotational movement of lower bar 89 relative to center link member 75 as shown by arrow B in FIG. 5.

First mechanical hinge 61 further comprises a threaded stop pin 103 which extends through slot 99 and screws into threaded hole 85 in center link member 75. Stop pin 103 extending through slot 99 and screwed into threaded hole 85 effectively limits the range of rotational movement of lower bar 89 relative to center link member 75 to the distance from end 100-1 to end 100-2. FIG. 7 shows the position of lower bar 89 relative to upper bar 63 with pin 103 at one end of slot 99 and FIG. 8 shows the position of lower bar 89 relative to upper bar 63 with pin 103 at the other end of slot 99.

As can be appreciated, pivotal movement of upper bar 63 relative to center link 75 and rotational movement of lower bar 89 relative to center link 75 are independent of one another.

Figure 9:
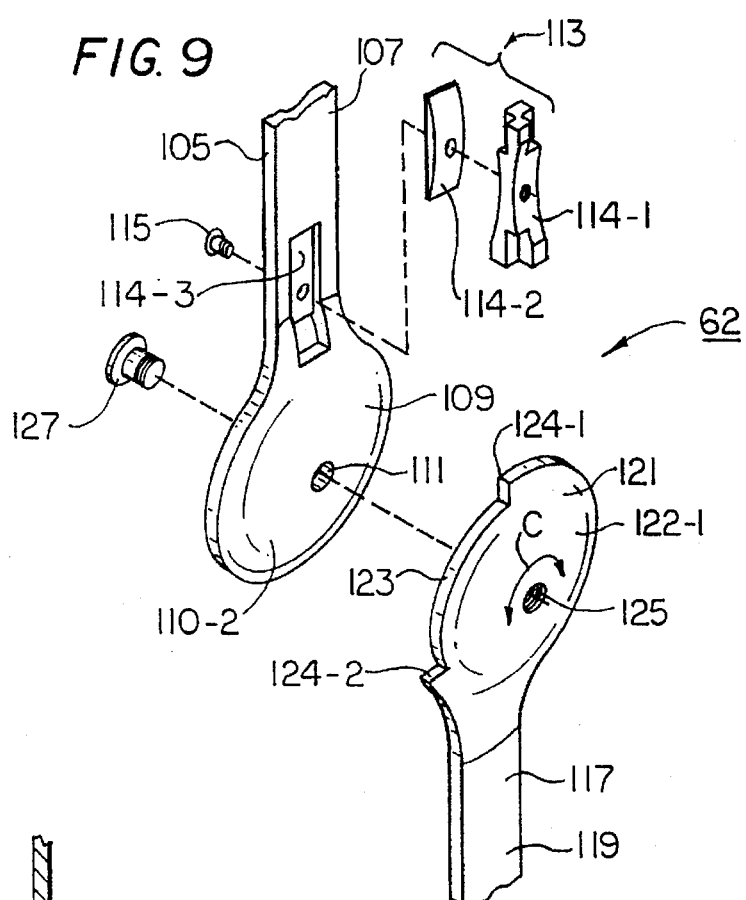
FIG. 9 is an exploded perspective view of the mechanical hinge on the lateral side of the knee in the knee brace shown in FIG. 1.
Figure 10:
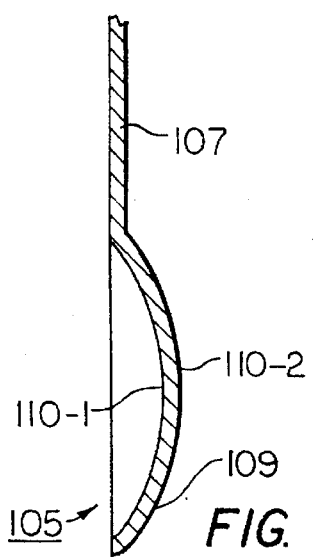
FIG. 10 is a fragmentary side view of the upper bar in the mechanical hinge shown in FIG. 9.
Figure 11:
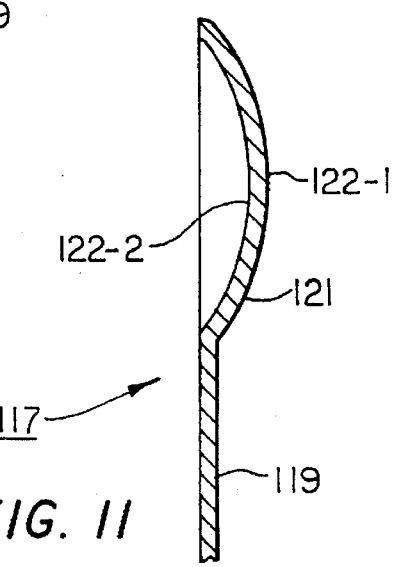

Second mechanical hinge 62, see also FIG. 9, comprises an upper bar 105 which is constructed of a material such as stainless steel or aircraft aluminum alloy. Upper bar 105 comprises an upper end 107 and a lower end 109. Upper end 107 is fixedly mounted on the lateral side of anterior femoral shell 13 by rivet 33 which secures buckle 37 to anterior femoral shell 13. Lower end 109 is disc shaped and includes a concave inner surface 110-1 and a convex outer surface 110-2. Lower end 109 has a hole 111 located approximately in the center thereof. Upper bar 105 also has a stop pin 113 having a front stop portion 114-1 and a rear stop portion 114-2. Stop pin 113 is removably mounted in a recess 114-3 at the juncture of upper end 105 and lower end 109 by a screw 115.

Second mechanical hinge 62 further comprises a lower bar 117. Lower bar 117 is constructed of a material such as stainless steel or aircraft aluminum alloy. Lower bar 117 comprises a lower end 119 and an upper end 121. Lower end 119 is fixedly mounted to the lateral side of posterior calf cuff 17 by the rivet 33 used to secure buckle 58 to posterior calf cuff 17. Upper end 121 is disc shaped and includes a concave inner surface 122-1 and a convex outer surface 122-1, concave inner surface 122-1 overlying convex outer surface 110-2 at the lower end 109 of upper bar 105. Upper end 121 has an edge 123 having a recess 123-1 having a first end 124-1 and a second end 124-2. Upper end 121 also has a threaded hole 125 approximately in the center thereof.

Second mechanical hinge 62 further comprises a threaded pivot pin 127 which extends through hole 111 and is screwed into threaded hole 125 so as pivotally interconnects upper bar 105 to lower bar 117. Pivot pin 127 enables for anterior-posterior movement of lower bar 117 relative to upper bar 105 in the direction as shown by arrow C in FIG. 9. Stop pin 113 in upper bar 105 is situated within recessed edge 123 of lower bar 117. Upon anterior-posterior movement of lower bar 117 relative to upper bar 105, stop pin 113 draws contact with lower bar 117 at first and second ends 124-1, 124-2 of recess 123-1 which effectively limit the range of anterior-posterior movement. Additionally, stop pin 113 can be replaced with a stop pin (not shown) of a different size (i.e. width) so as to create a different range of permissible anterior-posterior motion.

Knee brace 11 further comprises a pair of hinge pads 128, 129 removably mounted on the inner surface of first mechanical hinge 61 and second mechanical hinge 62, respectively. Hinge pads 128, 129 are manufactured of a soft material such as foam to increase the comfort of hinges 61 and 62 on the knee joint of the person.

As can be appreciated, a knee brace according to this invention can be made for the left leg of a person instead of the right leg by having hinge 61 still connected to anterior tibial shell 15 as in knee brace 11 but on the medial side of the knee of the left leg rather than the lateral side and hinge 62 connected to posterior calf cuff 17 as in knee brace 11 but on the lateral side of the knee of the left leg rather than the medial side.

Knee brace 11 may be attached to the leg of a person in the following manner. First, unfasten straps 34, 39, 53, and 59. Then fully straighten first mechanical hinge 61 and fully flex second mechanical hinge 62. Next, place knee brace 11 on the leg of the person, wrapping anterior femoral shell 13 properly around the thigh area of the person, wrapping anterior tibial shell 15 around the lower leg of the person, and wrapping posterior calf cuff 17 around the calf of the person. Proceed by aligning hinge pads 128, 129 with the medial and lateral sides, respectively, of the anatomical knee joint of the person. Then, with the leg in full extension, tighten strap 53 wrapping strap 53 around the back of the leg so that it sits comfortably above the calf muscle. Adjust knee brace 11 so that upper bars 63, 105 are positioned at the midline of the thigh medially and laterally, respectively.

Similarly, adjust knee brace 11 so that lower bars 89, 117 are positioned at the midline of the calf medially and laterally, respectively. Next, tighten strap 59 so that anterior tibial shell 15 rests firmly and comfortably against the leg of the person. Tighten strap 39 and then tighten strap 34. Once knee brace 11 is properly mounted on the leg of the person, brace 11 will flex and extend with anterior-posterior as well as internal rotational movement depending on the replication of the natural pattern of the knee joint in flexion and extension in the person wearing brace 11.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A knee brace for providing support for the knee of a person, comprising:
   a) an anterior femoral shell conforming to the shape of the upper leg of the person;
   b) an anterior tibial shell conforming to the shape of the lower leg of the person;
   c) a posterior calf cuff conforming to the shape of the lower leg of the person;
   d) a first mechanical hinge positionable on the medial side of the knee of the person, said first mechanical hinge comprising an upper bar having an upper end and a lower end and a lower bar having an upper end and a lower end, the upper end of the upper bar being fixedly mounted to said anterior femoral shell, the lower end of the lower bar being fixedly mounted to said anterior tibial shell, and the upper end of the lower bar being pivotly interconnected to the lower end of the upper bar so as to provide anterior-posterior movement of the lower bar relative to the upper bar and rotational movement of the lower bar relative to the upper bar;
   e) a second mechanical hinge positionable on the lateral side of the knee of the person, said second mechanical hinge comprising an upper bar having an upper end and a lower end and a lower bar having an upper end and a lower end, the upper end of the upper bar being fixedly mounted to said anterior femoral shell, the lower end of the lower bar being fixedly mounted to said posterior calf cuff, and the upper end of the lower bar being pivotly interconnected to the lower end of the upper bar so as to provide anterior-posterior movement of the lower bar relative to the upper bar;
   f) means for holding said anterior femoral shell in place on the upper leg of the person;
   g) means for holding said anterior tibial shell in place on the lower leg of the person; and
   h) means for holding said posterior calf cuff in place on the lower leg of the person.

2. The knee brace as claimed in claim 1 wherein the anterior-posterior movement in the first mechanical hinge and the rotational movement in the first mechanical hinge are independent of one another.

3. The knee brace as claimed in claim 2 wherein said first mechanical hinge comprises:
   a) an upper bar having an upper end and a lower end, the lower end having a hole;
   b) a center link member overlying the lower end of said upper bar, said center link having an inner surface, a convex outer surface, a first threaded hole, a second threaded hole and a third threaded hole;
   c) a first pivot pin extending through the hole in said upper bar and screwed into the first threaded hole in said center link member, so as to pivotally interconnect said center link member to said upper bar and provide thereby anterior-posterior movement of said center link member relative to said upper bar;
   d) a lower bar having an upper end and a lower end, the upper end having an outer surface and a concave inner surface, said concave inner surface at least partially overlying said convex outer surface of said center link member, the upper end of the lower bar having a hole and a slot;
   e) a second pivot pin extending through the hole in said lower bar and screwed into the second threaded hole in said center link member, said second pivot pin enabling rotational movement of said lower bar relative to said central link member; and
   f) a first stop pin extending through the slot in said lower bar and the third threaded hole in said center link member, said first stop pin limiting the range of internal rotational movement of said lower bar relative to said central link member.

4. The knee brace as claimed in claim 3, further comprising a second stop pin on the lower end of the upper bar, and wherein said center link member has an edge having a recess, the recess having a first end and a second end, the second stop pin being positioned within the recess in the edge of said center link member so that upon movement of said central link member relative to the upper bar, the second stop pin limits the range of movement of the upper bar relative to said center link member.

5. The knee brace as claimed in claim 4 wherein said second stop pin is removably mounted in said upper bar.

6. A mechanical hinge for use in a knee brace, comprising:
   a) an upper bar having an upper end and a lower end, the lower end having a hole to receive a first pivot pin;
   b) a center link member overlying the lower end of said upper bar, said center link having a convex outer surface, a first threaded hole, a second threaded hole and a third threaded hole;
   c) a first pivot pin extending through the hole to receive a first pivot pin in said upper bar and into the first threaded hole in said center link member, so as to pivotally interconnect said center link member to said upper bar and provide thereby anterior-posterior movement of said center link member relative to said upper bar,
   d) a lower bar having an upper end and a lower end, the upper end having a concave inner surface at least partially overlying said convex outer surface of said center link member, the upper end of the lower bar having a hole and a slot;
   e) a second pivot pin extending through the hole in said lower bar and into the second threaded hole in said center link member, said second pivot pin enabling rotational movement of said lower bar relative to said central link member; and f) a first stop pin extending through the slot in said lower bar and into the third threaded hole in said center link member, said first stop pin limiting the range of rotational movement of said lower bar relative to said central link member.

7. The mechanical hinge as claimed in claim 6, further comprising a second stop pin on the lower end of the upper bar, and wherein said center link member has an edge having a recess including a first end and a second end, the second stop pin being positioned within the recess of said center link member so that upon movement of said central link member relative to the upper bar, the second stop pin limits the range of movement of the upper bar relative to said center link member.

8. A mechanical hinge for use in a knee brace, comprising:

a) an upper bar having an upper end and a lower end;

b) a center link member overlying and pivotally mounted by a first connection means on the lower end of said upper bar for providing anterior-posterior movement of said center link member relative to said upper bar, said center link member having a convex outer surface; and c) a lower bar having an upper end and a lower end, the upper end having a concave inner surface overlying said convex outer surface of said center link member and pivotally mounted by a second connection means independent of said first connection means thereon so as to provide rotational movement of said center link member relative to said lower bar.

9. The mechanical hinge as claimed in claim 8 further comprising a slot and pin arrangement for limiting rotational movement of said center link member relative to said lower bar.

* * * * *